United States Patent [19]
Collis

[11] 3,984,890
[45] Oct. 12, 1976

[54] ELECTRIC TOOTH BRUSH

[76] Inventor: George C. Collis, 313 W. 48th St., Minneapolis, Minn. 55409

[22] Filed: June 25, 1975

[21] Appl. No.: 590,399

[52] U.S. Cl............................................. 15/22 R
[51] Int. Cl.²..................................... A46B 13/02
[58] Field of Search.................... 15/22 R, 22 A; 128/62 R, 62 A

[56] References Cited
UNITED STATES PATENTS

| | | | |
|---|---|---|---|
| 2,282,700 | 5/1942 | Bobbroff............................. | 15/22 R |
| 3,284,829 | 11/1966 | Allen.................................. | 15/22 R |
| 3,732,589 | 5/1973 | Burki................................. | 15/22 R |

*Primary Examiner*—Edward L. Roberts
*Attorney, Agent, or Firm*—John W. Adams

[57] ABSTRACT

This is an electro-mechanical tooth brush having opposed sets of bristles specifically designed to simultaneously brush both the inner and outer surfaces of the teeth by reciprocating one set back and forth, and also having a central hub element for brushing the chewing surfaces of the teeth fixed to and moving with the reciprocating set of bristles.

3 Claims, 3 Drawing Figures

U.S. Patent  Oct. 12, 1976  3,984,890
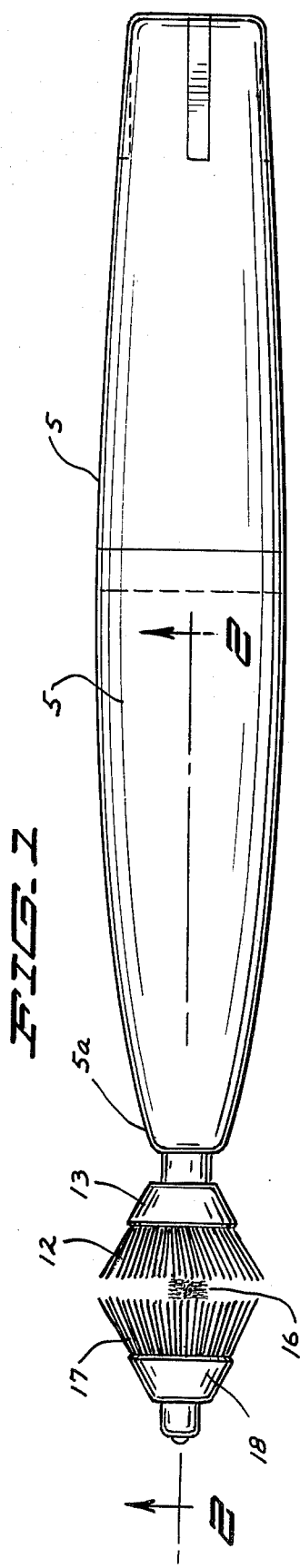
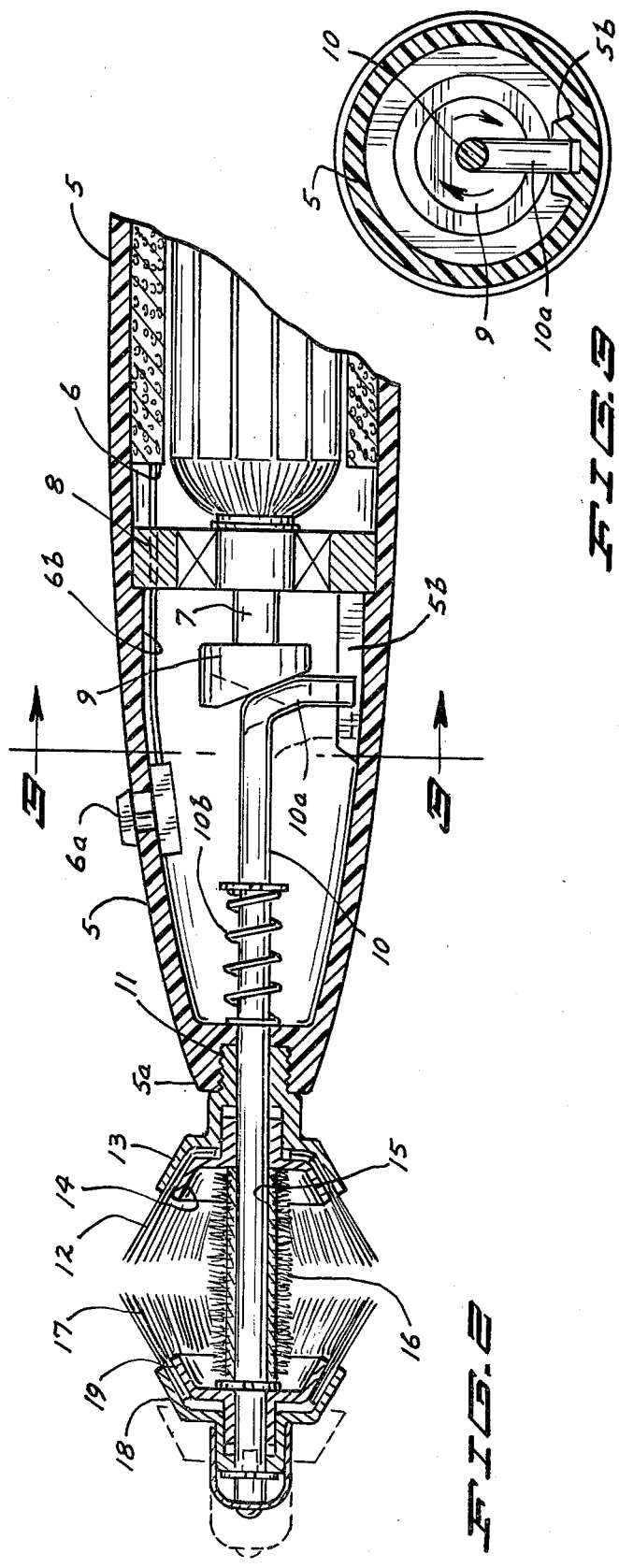

ELECTRIC TOOTH BRUSH

It is an object of the present invention to provide an electro-mechanical tooth brush specifically designed to simultaneously brush both the inner and outer tooth surfaces of either or both of the upper and lower rows of teeth.

More specifically it is an object to provide an electrically actuated tooth brush which is specifically constructed to simultaneously brush the inner and outer surfaces of both the upper and lower rows of teeth and also brush the chewing surfaces of the teeth at the same time.

These and other objects and advantages of this invention will more fully appear in the following description made in connection with the accompanying drawings in which like reference characters refer to similar parts throughout the several views, and in which:

FIG. 1 is a top plan view of a tooth brush embodying this invention;

FIG. 2 is a fragmentary vertical sectional view taken substantially along the line 2—2 of FIG. 1; and FIG. 3 is a transverse sectional view taken substantially along the line 3—3 of FIG. 2.

The tooth brush illustrated in the accompanying drawings embodies an outer casing 5 having an electric motor 6 mounted therein for driving the rotary drive shaft 7 journaled in a suitable bearing 8 mounted in said casing 5. A rotary cam 9 is fixed to the end of the shaft 7 and actuates a reciprocating pin or rod 10 mounted for back and forth movement in a suitable bushing 11 provided at the forward end 5a of the casing 5.

Two sets of opposed bristles 12 and 17 are provided and in the form shown the bristles 12 (closest to the end 5a of casing 5) forms the stationary set. The stationary bristles 12 are conically shaped and are mounted in fixed relation adjacent the forward end 5a of the casing 5. These bristles 12 are clamped between a pair of conically shaped mounting elements 13 and 14 and extend outwardly therefrom in diverging relationship to the reciprocating rod 10.

A bristle mounting sleeve 15 is fixed to the rod 10 for back and forth reciprocation therewith and has biting surface reciprocating bristles 16 mounted in substantially cyclindrical relationship therearound.

In the form shown the bristles 17 are conically shaped and are clamped between a pair of mounting members 18 and 19 which are fixed to the outer end portion of the rod 10 for reciprocation therewith. Said reciprocating bristles 17 are generally opposed to the stationary bristles 12.

The electric motor 6 may have any conventional source of electricity (not shown) such as batteries or plug-in type cord. A switch 6a is provided and wires 6b connect said source (not shown) with the motor 6 through said switch 6a in the conventional manner. The inner end of the reciprocating rod 10 has a cam follower 10a provided thereon such as by forming a bend in the rod as illustrated. A spring 10b holds the follower 10a in contact with the cam 9 and the end of the bend 10a rides in a track or channel 5b formed on the inside of the casing 5, as best shown in FIG. 3.

Reciprocating actuation of the rod 10 by the cam mechanism illustrated moves the reciprocating bristles 16 and 17 back and forth against the tooth surfaces simultaneously with the brushing contact produced by moving the stationary bristles 12 against the outer surfaces of the teeth. The cylindrical bristles 16 brush the biting surfaces of both rows of teeth simultaneously with the cleaning of both the inner and outer surfaces thereof by the bristles 16 and 17.

It will, of course, be understood that various changes may be made in the form, details, arrangement and proportions of the parts without departing from the scope of this invention as set forth in the appended claims.

What is claimed is:

1. An electro-mechanically reciprocated tooth brush comprising,
   a casing,
   an electric motor housed within said casing,
   a reciprocating rod slidably mounted at one end of casing for back and forth movement therein,
   means associated with said electric motor and said casing for producing back and forth reciprocation of said rod when said motor is energized,
   stationary bristles concentrically surrounding the axis of said rod in radially outwardly spaced relation thereto and mounted in fixed relation to said end of said casing,
   reciprocating bristles fixed to said rod in generally opposed relation to said stationary bristles for back and forth movement relative to said stationary bristles to simultaneously brush the inner and outer surfaces of the teeth positioned between said stationary and reciprocating bristles.

2. The structure set forth in claim 1 and a sleeve fixed to said rod and positioned between said bristles and having cylindrical bristles fixed thereto for reciprocation with said rod to simultaneously brush the biting surfaces of the teeth during brushing of the inner and outer surfaces.

3. The structure set forth in claim 2 wherein said reciprocating bristles are disposed further from said casing than said stationary bristles.

* * * * *